(12) United States Patent
Snyder et al.

(10) Patent No.: US 7,094,604 B2
(45) Date of Patent: Aug. 22, 2006

(54) PRODUCTION OF PSEUDOTYPED RECOMBINANT AAV VIRIONS

(75) Inventors: Richard O. Snyder, Gainesville, FL (US); Sergei Zolotukhin, Gainesville, FL (US); Yoshihisa Sakai, Gainesville, FL (US); Barry J. Byrne, Gainesville, FL (US); Mark R. Potter, Gainesville, FL (US); Irine Zolotukhin, Gainesville, FL (US); Scott Loiler, Gainesville, FL (US); Vince A. Chiodo, Gainesville, FL (US); Nicholas Muzyczka, Gainesville, FL (US); William W. Hauswirth, Gainesville, FL (US); Terence R. Flotte, Alachua, FL (US); Corinna Burger, Gainesville, FL (US); Edgardo Rodriguez, Gainesville, FL (US); Kevin R. Nash, Gainesville, FL (US); Thomas J. Fraites, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 0 days.

(21) Appl. No.: 10/798,192

(22) Filed: Mar. 11, 2004

(65) Prior Publication Data

US 2004/0209245 A1  Oct. 21, 2004

Related U.S. Application Data

(63) Continuation of application No. 10/456,423, filed on Jun. 5, 2003, now abandoned.

(60) Provisional application No. 60/385,864, filed on Jun. 5, 2002.

(51) Int. Cl.
*C12N 5/10* (2006.01)
*C12N 15/864* (2006.01)
*C12N 15/35* (2006.01)

(52) U.S. Cl. .................. 435/457; 435/325; 435/320.1; 435/455; 435/456; 536/23.1; 536/23.72; 536/24.1

(58) Field of Classification Search ............ 435/320.1, 435/325, 366; 536/23.1, 23.2, 23.5, 23.7, 536/23.72, 24.1
See application file for complete search history.

(56) References Cited

U.S. PATENT DOCUMENTS

| 6,491,907 B1 * | 12/2002 | Rabinowitz et al. ........ 424/93.2 |
| 2002/0045264 A1 | 4/2002 | During et al. |
| 2003/0223966 A1 * | 12/2003 | Fraites et al. .............. 424/93.2 |
| 2005/0014262 A1 * | 1/2005 | Gao et al. .................... 435/456 |

OTHER PUBLICATIONS

Zolotukhin et al., Methods, 2002, vol. 28, pp. 158-167.*
Bowles, D. et al.: Marker Rescue of Adeno-Associated Virus (AAV) Capsid Mutants: a Novel Approach for Chimeric AAV Production. Journal of Virology. Jan. 2003, vol. 77, No. 1, pp. 423-432.
Cao, L. et al.: Replication Competent Helper Functions for Recombinant AAV Vector Generation. Gene Therapy. 2002, vol. 9, pp. 1199-1206.
Mendelson, E. et al.: Identification of the trans-Acting Rep Proteins of Adeno-Associated Virus by Antibodies to a Synthetic Oligopeptide. Journal of Virology. Dec. 1986, vol. 60, No. 3, pp. 823-832.

* cited by examiner

*Primary Examiner*—David Guzo
(74) *Attorney, Agent, or Firm*—Nicholas A. Zachariades

(57) ABSTRACT

Vectors that encode Adeno-Associated Virus (AAV) Rep and Cap proteins of different serotypes and Adenovirus transcription products that provide helper functions were used to produce pseudotyped recombinant AAV (rAAV) virions. Purification methods generated pseudotyped rAAV virion stocks that were 99% pure with titers of $1\times10^{12}$–$1\times10^{13}$ vector genomes/ml.

35 Claims, 5 Drawing Sheets

```
                          SEQUENCE LISTING

<160> NUMBER OF SEQ ID NOS: 4

<210> SEQ ID NO 1
<211> LENGTH: 28
<212> TYPE: DNA
<213> ORGANISM: Artificial
<220> FEATURE:
<223> OTHER INFORMATION: Synthetic Oligonucleotide

<400> SEQUENCE: 1
gagcaataaa tgatttaaac caggtatg                                      28

<210> SEQ ID NO 2
<211> LENGTH: 32
<212> TYPE: DNA
<213> ORGANISM: Artificial
<220> FEATURE:
<223> OTHER INFORMATION: Synthetic Oligonucleotide

<400> SEQUENCE: 2
gctctagacc cgatgacgta agtcttttat cg                                 32

<210> SEQ ID NO 3
<211> LENGTH: 52
<212> TYPE: DNA
<213> ORGANISM: Artificial
<220> FEATURE:
<223> OTHER INFORMATION: Synthetic Oligonucleotide

<400> SEQUENCE: 3
cgcaataaag aacagtaaat aatttaaata gtcatgtctt tgttgatca cc            52

<210> SEQ ID NO 4
<211> LENGTH: 52
<212> TYPE: DNA
<213> ORGANISM: Artificial
<220> FEATURE:
<223> OTHER INFORMATION: Synthetic Oligonucleotide

<400> SEQUENCE: 4
ggtgatcaac aaaagacatg actatttaaa ttatttactg ttctttattg gc           52
```

US 7,094,604 B2

PRODUCTION OF PSEUDOTYPED RECOMBINANT AAV VIRIONS

CROSS-REFERENCE TO RELATED APPLICATIONS

The present application is a continuation of U.S. patent application Ser. No. 10/456,423 filed on Jun. 5, 2003 now abandoned which claims the priority of U.S. provisional patent application No. 60/385,864 filed on Jun. 5, 2002.

STATEMENT AS TO FEDERALLY SPONSORED RESEARCH

This invention was made with United States government support under grant numbers NS36302, HL51811, DK58327, and HL59412 all awarded by the National Institutes of Health. The United States government may have certain rights in the invention.

FIELD OF THE INVENTION

The invention relates to the fields of molecular biology, gene therapy, microbiology and virology. More particularly, the invention relates to compositions and methods for producing and purifying recombinant Adeno-Associated Virus (rAAV) virions.

BACKGROUND OF THE INVENTION

AAV, a non-pathogenic, helper-dependent virus, is an attractive vector for gene therapy as it exhibits a wide host and tissue range and is able to replicate in cells from any species as long as there is a successful infection of such cells with a suitable helper virus [e.g., Adenovirus (Ad) or Herpesvirus]. The host and tissue tropism of AAV is determined by the ability of its capsid to bind to specific cellular receptors and/or co-receptors. Due to the broad host and tissue range, however, delivery of conventional AAV preferentially to a particular tissue of interest has been problematic.

AAV of several different serotypes are known. Of these, serotype 2 AAV has been the most extensively studied and characterized. Accordingly, serotype 2 rAAV vectors (i.e., nucleic acid constructs) and virions (i.e., encapsidated vectors) have been proposed as the vector of choice for gene transfer protocols. Animal experiments, however, have shown that dramatic differences exist in the transduction efficiency and cell specificity of rAAV virions of different serotypes (Chao et al., Mol. Ther. 2:619–623, 2000; Davidson et al., PNAS 97:3428–3432, 2000; and Rabinowitz et al., J. Virol. 76:791–801, 2002). For example, non-serotype 2 AAV virions were able to transduce certain tissues more efficiently and specifically than serotype 2 virions. Accordingly, an AAV virion including a well-characterized serotype 2 genome and a non-serotype 2 capsid would be useful for certain tissue-specific gene transfer applications. Methods that facilitate preparing such pseudotyped AAV virions would also be useful. Current methods involve the use of multiple vectors to provide the replication, packaging, and helper functions that are required for the formation of recombinant virions. These methods are inefficient and inadequate for large-scale production of pseudotyped recombinant virions.

SUMMARY

The invention relates to the development of reagents and methods for producing purified AAV2 vectors pseudotyped with a non-serotype 2 AAV capsid. AAV helper vectors were constructed for pseudotyping AAV serotype 2 DNA with capsids from AAV serotypes 1 and 5. These helper vectors encode AAV gene products necessary for AAV virion production (i.e., Rep and Cap proteins), as well as transcription products having Ad helper function. To pseudotype AAV serotype 2 DNA with an AAV1 capsid, a helper vector encoding a serotype 2 Rep protein and a serotype 1 Cap protein was used. Similarly, a helper vector useful for pseudotyping AAV serotype 2 DNA with an AAV5 capsid encodes a serotype 2 Rep protein and a serotype 5 Cap protein. To purify pseudotyped virions, methods were developed that result in highly purified and concentrated virion stocks. These methods involve applying a virus-containing sample to an iodixanol gradient centrifugation step followed by a chromatography step. The helper vectors and purification methods described herein provide for efficient, large-scale production of pseudotyped virions without the need for multiple helper vectors. The resultant pseudotyped virions can be used in numerous gene therapy applications.

Accordingly, the invention features a nucleic acid molecule including a first nucleotide sequence encoding an AAV Rep protein of a first serotype, a second nucleotide sequence encoding an AAV Cap protein of a second serotype, the second serotype being different from the first serotype, and a third nucleotide sequence encoding a transcription product having at least one Adenoviral helper function. The nucleic acid molecule can be within a vector.

The AAV Rep protein can be an AAV serotype 2 protein. The AAV serotype 2 Rep protein can be a Rep52 protein and/or a Rep78 protein. Both Rep52 and Rep78 proteins can be encoded by the first nucleotide sequence.

The AAV Cap protein can be an AAV serotype 1 protein and/or an AAV serotype 5 Cap protein. The second nucleotide sequence encoding an AAV Cap protein can encode an AAV protein such as VP1, VP2, or VP3. The second nucleotide sequence can encode all three AAV Cap proteins VP1, VP2, and VP3. The transcription product having at least one Adenoviral helper function can be Adenovirus DNA binding protein, Adenovirus E4 protein, as well as Adenovirus virus associated RNA molecule.

The nucleic acid can be operably linked to at least one expression control sequence. The first nucleotide sequence encoding an AAV Rep protein of a first serotype can be operably linked to a promoter. Examples of promoters include AAV p5 and AAV p19 promoters. The second nucleotide sequence encoding an AAV Cap protein of a second serotype can also be operably linked to a promoter, such as an AAV p40 promoter. The third nucleotide sequence encoding a transcription product having at least one Adenoviral helper function can further be operably linked to a promoter. The nucleic acid molecule can further include a selectable marker such as a selectable marker that confers antibiotic resistance to a cell.

In another aspect, the invention features a cell including a nucleic acid molecule that includes a first nucleotide sequence encoding an AAV Rep protein of a first serotype, a second nucleotide sequence encoding an AAV Cap protein of a second serotype, the second serotype being different from the first serotype, and a third nucleotide sequence encoding a transcription product having at least one Adenoviral helper function. The cell can be a mammalian cell. The cell can further include a second nucleic acid that includes a polynucleotide (to be expressed) interposed between a first AAV inverted terminal repeat and a second AAV inverted terminal repeat. The second nucleic acid can be within a vector. The first and second AAV inverted terminal repeats can be AAV serotype 2 inverted terminal repeats. The polynucleotide can encode a protein or a selectable marker such as green fluorescent protein.

In still another aspect, the invention features a method of producing rAAV virions. The method includes the steps of placing a cell having: 1) a nucleic acid molecule that includes a first nucleotide sequence encoding an AAV Rep protein of a first serotype, a second nucleotide sequence encoding an AAV Cap protein of a second serotype, the second serotype being different from the first serotype, and a third nucleotide sequence encoding a transcription product having at least one Adenoviral helper function and 2) a nucleic acid having a polynucleotide to be expressed interposed between a first AAV inverted terminal repeat and a second AAV inverted terminal repeat under conditions in which the first nucleic acid molecule is expressed, the second nucleic acid molecule is replicated, and rAAV virions are produced, and isolating the rAAV virions produced from the cell. The cell can be a mammalian cell. The step of placing the cell under conditions in which the first nucleic acid molecule is expressed and the second nucleic acid molecule is replicated includes placing the cell into a culture medium. The step of isolating the rAAV virions produced from the cell includes separating the cell from the medium, lysing the cell to yield a cell lysate, and then isolating the rAAV virions from the cell lysate. This step can also include subjecting the produced rAAV virions to an iodixanol step gradient and can further include subjecting the produced rAAV virions to ion exchange chromatography. The produced rAAV virions can contain at least one AAV serotype 1 capsid protein or at least one AAV serotype 5 capsid protein.

Unless otherwise defined, all technical terms used herein have the same meaning as commonly understood by one of ordinary skill in the art to which this invention belongs. Commonly understood definitions of molecular biology terms can be found in Rieger et al., Glossary of Genetics: Classical and Molecular, 5th edition, Springer-Verlag: New York, 1991; and Lewin, Genes V, Oxford University Press: New York, 1994. Commonly understood definitions of virology terms can be found in Granoff and Webster, Encyclopedia of Virology, 2nd edition, Academic Press: San Diego, Calif., 1999; and Tidona and Darai, The Springer Index of Viruses, 1st edition, Springer-Verlag: New York, 2002. Commonly understood definitions of microbiology can be found in Singleton and Sainsbury, Dictionary of Microbiology and Molecular Biology, 3rd edition, John Wiley & Sons: New York, 2002.

By the term "gene" is meant a nucleic acid molecule that codes for a particular protein, or in certain cases a functional or structural RNA molecule.

As used herein, a "nucleic acid," "nucleic acid molecule," or "polynucleotide" means a chain of two or more nucleotides such as RNA (ribonucleic acid) and DNA (deoxyribonucleic acid).

As used herein, "protein" or "polypeptide" are used synonymously to mean any peptide-linked chain of amino acids, regardless of length or post-translational modification, e.g., glycosylation or phosphorylation.

When referring to a nucleic acid molecule or polypeptide, the term "native" refers to a naturally-occurring (e.g., a wild-type; "WT") nucleic acid or polypeptide.

By the term "Rep protein" is meant a polypeptide having at least one functional activity of a native AAV Rep protein (e.g., Rep 40, 52, 68, 78). By the term "Cap protein" is meant a polypeptide having at least one functional activity of a native AAV Cap protein (e.g., VP1, VP2, VP3). A "functional activity" of a protein is any activity associated with the physiological function of the protein. For example, functional activities of Rep proteins (e.g., Rep 40, 52, 68, 78) include facilitating replication of DNA through recognition, binding and nicking of the AAV origin of DNA replication as well as DNA helicase activity. Additional functions include modulation of transcription from AAV (or other heterologous) promoters and site-specific integration of AAV DNA into a host chromosome. Examples of functional activities of Cap proteins (e.g., VP1, VP2, VP3) include the ability to induce formation of a capsid, facilitate accumulation of single-stranded DNA, facilitate AAV DNA packaging into capsids (i.e., encapsidation), bind to cellular receptors, and facilitate entry of the virion into host cells.

As used herein, the term "vector" refers to a nucleic acid molecule capable of transporting another nucleic acid to which it has been linked. Vectors capable of directing the expression of genes to which they are operatively linked are referred to herein as "expression vectors."

A first nucleic acid sequence is "operably" linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked nucleic acid sequences are contiguous and, where necessary to join two protein coding regions, in reading frame.

As used herein, the phrase "expression control sequence" refers to a nucleic acid that regulates the replication, transcription and translation of a coding, sequence in a recipient cell. Examples of expression control sequences include promoter sequences, polyadenylation (pA) signals, introns, transcription termination sequences, enhancers, upstream regulatory domains, origins of replication, and internal ribosome entry sites ("IRES"). The term "promoter" is used herein to refer to a DNA regulatory sequence to which RNA polymerase binds, initiating transcription of a downstream (3' direction) coding sequence.

By the term "pseudotyped" is meant a nucleic acid or genome derived from a first AAV serotype that is encapsidated or packaged by an AAV capsid containing at least one AAV Cap protein of a second serotype (i.e., one different from the first AAV serotype).

By "AAV inverted terminal repeats", "AAV terminal repeats", "ITRs", and "TRs" are meant those sequences required in cis for replication and packaging of the AAV virion including any fragments or derivatives of an ITR which retain activity of a full-length or WT ITR.

As used herein, the terms "rAAV vector" and "recombinant AAV vector" refer to a recombinant nucleic acid derived from an AAV serotype, including without limitation, AAV1, AAV2, AAV3, AAV4, AAV5, AAV6, AAV7, etc. rAAV vectors can have one or more of the AAV WT genes deleted in whole or in part, preferably the rep and/or cap genes, but retain functional flanking ITR sequences. A "recombinant AAV virion" or "rAAV virion" is defined herein as an infectious, replication-defective virus composed of an AAV protein shell encapsulating a heterologous nucleotide sequence that is flanked on both sides by AAV ITRs.

By the term "rAAV1" is meant a rAAV virion having at least one AAV serotype 1 capsid protein. Similarly, by the term "rAAV5" is meant a rAAV virion having at least one AAV serotype 5 capsid protein.

Although methods and materials similar or equivalent to those described herein can be used in the practice or testing of the present invention, suitable methods and materials are described below. All publications, patent applications, patents and other references mentioned herein are incorporated by reference in their entirety. In the case of conflict, the present specification, including definitions will control. The particular embodiments discussed below are illustrative only and not intended to be limiting.

DETAILED DESCRIPTION

Figure 1:
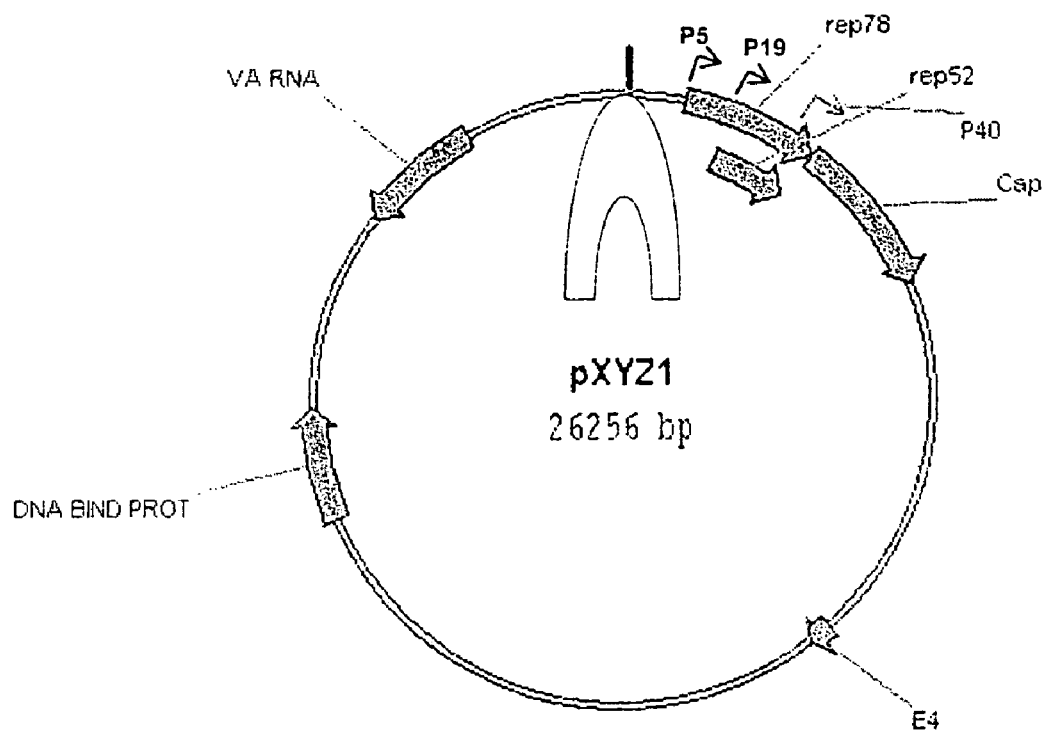
FIG. 1 is two plasmid maps (top:pXYZ1, bottom: pXYZ5).
Figure 1:
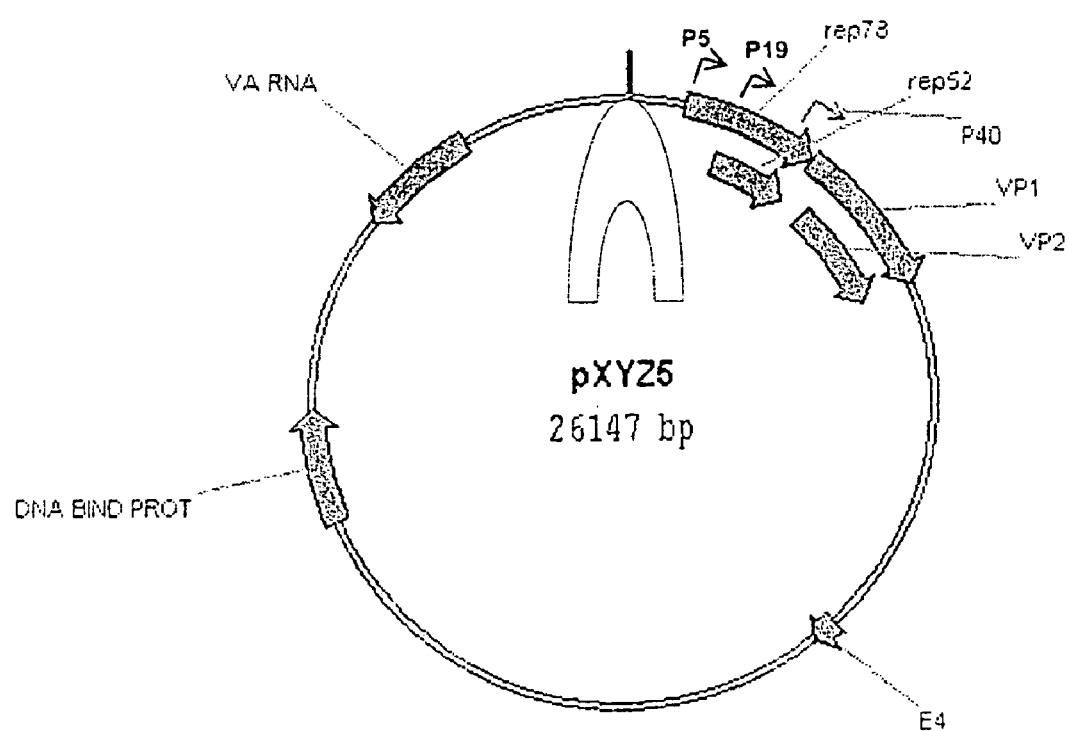
Figure 2:
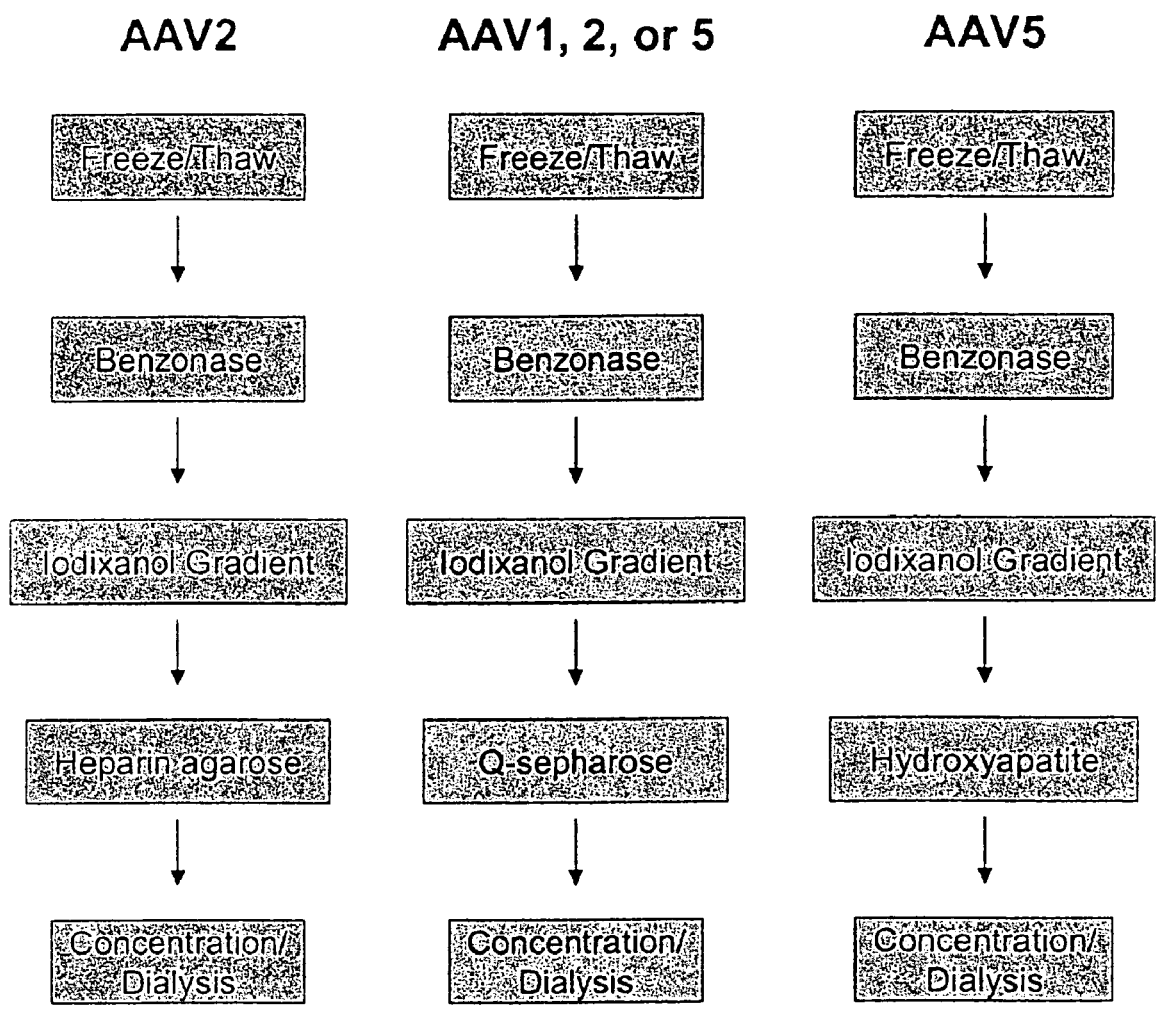
FIG. 2 is a schematic illustration of purification schemes for rAAV1, 2, and 5 virions.

The invention provides methods and compositions for producing pseudotyped AAV virions. In the examples described below, purified pseudotyped rAAV virions were produced in large quantities by introducing into host cells both (1) a first nucleic acid construct that contains AAV ITRs of a first AAV serotype, and encodes an exogenous nucleic acid (i.e., polynucleotide to be expressed in a cell infected with the virions produced); and (2) a second nucleic acid construct that encodes Ad transcription products having Ad helper function, Rep proteins of the first serotype, and Cap proteins of a second serotype.

In the first nucleic acid construct, the exogenous nucleic acid is located between two AAV ITRs that are the minimal cis-acting AAV sequences that direct replication and packaging of an AAV genome as well as an rAAV vector. The second nucleic acid construct has sequences that encode (1) at least one AAV Cap protein of a first serotype, (2) at least one AAV Rep protein of a second serotype (i.e., serotype of the rAAV vector to be encapsidated), and (3) at least one transcription product having Ad helper function.

The first and second nucleic acids are introduced into host cells, which are then cultured under appropriate conditions to allow the host cells to replicate. During this phase, the portion of the first nucleic acid construct containing the two AAV ITRs and exogenous nucleic acid (i.e., rAAV vector) is replicated, resulting in the generation of many rAAV vectors; the second nucleic acid construct is expressed, resulting in the production of transcription products having Ad helper function as well as Rep and Cap proteins. Ad proteins such as E2A and E4, as well as Ad VA RNA provide helper functions that facilitate a productive AAV infection. Rep proteins (e.g., Rep40, Rep52, Rep68, Rep78) are essential for rAAV vector replication, while the Cap (e.g., VP1, VP2, VP3) proteins are structural proteins that are required for formation of the virion capsid. As a result of expressing capsid proteins in the presence of the replicated vectors, the replicated rAAV vectors of a first serotype (e.g., serotype 2) are packaged into infectious rAAV virions (i.e., an infectious virus particle containing an rAAV vector) containing cap proteins of a second serotype (e.g., serotypes 1, 5).

The below described preferred embodiments illustrate adaptations of these compositions and methods. Nonetheless, from the description of these embodiments, other aspects of the invention can be made and/or practiced based on the description provided below.

Biological Methods

Methods involving conventional molecular biology techniques are described herein. Such techniques are generally known in the art and are described in detail in methodology treatises such as Molecular Cloning, 3rd edition, Sambrook and Russell, Cold Spring Harbor Press, 2001; and Current Protocols in Molecular Biology, ed. Ausubel et al., Greene Publishing and Wiley-Interscience, New York, 1992 (with periodic updates). Methods for chemical synthesis of nucleic acids are discussed, for example, in Beaucage and Carruthers, Tetra. Letts. 22:1859–1862, 1981, and Matteucci et al., J. Am. Chem. Soc. 103:3185, 1981. Nucleic Acid Constructs That Encode An Exogenous Nucleic Acid And Nucleic Acids That Encode Rep Proteins, Cap Proteins, and Transcription Products Having Ad Helper Function.

The first nucleic acid construct described above includes an exogenous nucleic acid and also contains other sequences that facilitates expression of the exogenous nucleic acid in a host cell. An exogenous nucleic acid is a nucleic acid that is not native to AAV. The exogenous nucleic acid is inserted into the construct in such a way that the nucleic acid is expressed. For example, the nucleic acid is placed within a construct (e.g., vector) at a particular location such that: (1) it is between two functional AAV ITRs of a particular serotype, (2) it is operatively linked with a promoter and (3) it is placed 5' to a pA tail.

The exogenous nucleic acid can be any nucleic acid that is desired to be included in the rAAV to be produced so long as it does not exceed the number of nucleotides that can be encapsulated within a rAAV virion (i.e., approximately 5 kilobases). Typical examples of such nucleic acids include those that encode a protein or an RNA. Proteins might, for example, be those that exert a therapeutic effect on a diseased cell (e.g., a human or non-human cell). Genes that can be delivered by rAAV to exert a therapeutic effect include alpha-one antitrypsin, clotting factor IX, clotting factor VIII, clotting factor VII, dystrophin, $\alpha$-,$\beta$-,$\delta$-,$\epsilon$-sarcoglycans, tyrosine hydroxylase, aromatic acid decarboxylase, GTP cyclohydrolasel, erythropoietin, aspartoacylase (ASPA), Nerve growth factor (NGF), lysosomal betaglucuronidase (GUSB), insulin, alpha-synuclein, basic fibroblast growth factor (FGF-2), IGF1, alpha-galactosidase A (alpha-gal A), neurotrophin-3, Neuroglobin (Ngb), angoigenic proteins (vascular endothelial growth factor (VEGF165)), anti-angiogenic proteins, and any cytokines, including interferons (IFN-α, IFN-β, IFN-γ), interleukins, GM-CSF (granulocyte-macrophage colony-stimulating factor), M-CSF (macrophage colony-stimulating factor), tumor necrosis factors, growth factors (TGF-β (transforming growth factor-β), IL-10, IL-13, IL-4, and PDGF (platelet-derived growth factor)) or neurotrophic factors CNTF (ciliary Neurotrophic factor), brain-derived neurotrophic factor (BDNF), and GDNF (glial cell line derived neurotrophic factor). Alternatively, proteins might be those that act as reporters or markers of gene expression (e.g., GFP, β-galactosidase, luciferase). RNA may be anti-sense, RNAi, and ribozymes.

The second nucleic acid construct encodes transcription products having Ad helper function and AAV proteins that facilitate pseudotyping of an rAAV vector. Such a nucleic acid construct encodes: 1) at least one AAV Cap protein of a first serotype, 2) at least one AAV Rep protein of a second serotype (i.e., serotype of the rAAV vector to be encapsidated), and, 3) at least one transcription product having Ad helper function. A nucleic acid encoding a Rep and/or Cap protein and transcription product having Ad, helper function is inserted into the second nucleic acid construct in such a way that the nucleic acid is expressed. For example, the nucleic acid is placed within a construct. (e.g., vector) at a particular location such that: (1) it is operatively linked with a promoter and (2) it is placed 5' to a pA tail.

A nucleic acid encoding a Cap protein is any nucleic acid that encodes at least one functional Cap protein or functional derivative thereof. The AAV cap gene encodes three capsid proteins: VP1, VP2 and VP3, and any one or combination of these three proteins may be expressed by a nucleic acid of the invention. A nucleic acid encoding a Rep protein is any nucleic acid that encodes at least one functional Rep protein or functional derivative thereof. Any one or combination of the four AAV Rep proteins Rep40, Rep52, Rep68, and Rep78, may be expressed by a nucleic acid of the invention. The rep and cap genes used in methods of the invention can be mutant or non-naturally occurring versions of AAV rep and cap genes. For example, nucleic acids encoding Rep and Cap proteins useful in the invention may be hybrid sequences containing portions of rep and cap genes from different serotypes. Furthermore, rep and cap genes used in compositions and methods of the invention may include engineered as well as naturally-occurring rep and cap mutants. A preferred rep gene according to the invention is a serotype 2 rep gene, while a preferred cap gene is a serotype 1 or 5 cap gene. A nucleic acid encoding a transcription product having Ad helper function is any nucleic acid that encodes at least one protein or RNA molecule having Ad helper function. Ad gene products that are known to provide Ad helper function include E1a, E1b, E2a, E4 (e.g., E4orf6) and VA RNA. Such nucleic acids can be mutant or non-naturally occurring versions of Ad nucleotide sequences. Mutants include those that are engineered as well as those that are naturally-occurring.

In the experiments described below, vectors for pseudotyping rAAV virions (e.g., AAV helper plasmids) are constructed by combining the ORF coding for AAV Rep proteins of a first serotype and the ORF coding for capsid proteins of serotypes different from the first (FIG. 1). To generate a rAAV2 vector pseudotyped with an AAV1 capsid, for example, a helper plasmid such as pACG2R1C is constructed by substituting the AAV1 cap ORF for AAV2 cap ORF in pACG2 (Li et al., J. Virol. 71:5236–5243, 1997). Similarly, to generate a rAAV2 vector pseudotyped with an AAV5 capsid, a helper plasmid such as pACG2R5C can be constructed. Rep2cap1 and rep2cap5 helper sequences resulting from these constucts can be subcloned into an Ad helper plasmid, pXYZ, constructed from pAdEasy (Stratagene). To construct pXYZ, several Ad genes (penton, core protein, hexon, and Ad DNA polymerase) are disrupted and the left hand end of the Ad genome is removed to eliminate the possibility of generating infectious Ad and Ad structural proteins (some of which are cytotoxic). The resultant plasmids pXYZ1 (26,256 bp) and pXYZ5 (26,147 bp) (FIG. 1) encode the AAV proteins and Ad transcription products required to pseudotype AAV2-ITR-containing nucleic acids into AAV1 and AAV5 capsids. Both plasmids contain the Ad VA, E2A and E4 genes under the transcriptional control of their native promoters. Both plasmid backbones also encode for ampicillin resistance. Additionally, rAAV vectors pseudotyped with AAV1 and AAV5 capsids can be generated using plasmids pACG2R1C and pACG2R5C, respectively, with plasmids pXX6 and pXYZ. See Xiao et al., J. Virol. 72:2224–2232, 1998.

Alternatively, the AAV and Ad transcription products can be expressed by more than one vector. For example, cells can be cotransfected with a first vector expressing the AAV genes and a second vector expressing transcription products. In another example, the AAV proteins and Ad transcription products can be expressed by three different vectors. In this method, cells are transfected with the three vectors expressing the AAV proteins and Ad transcription products. In some applications, cells can be transfected with more than one vector expressing the AAV and Ad genes and a rAAV vector.

In preferred applications, the exogenous nucleic acid and the nucleic acids encoding Rep, Cap and transcription products having Ad helper function are operably linked to one or more expression control sequences that facilitate gene expression in host cells. Generally, operably linked nucleic acid sequences are contiguous and, where necessary to join two protein coding regions, in reading frame. Examples of expression control sequences include promoters, insulators, response elements, introns, IRESs, silencers, enhancers, introns, initiation sites, termination signals, and pA tails. Within the invention, any expression control sequence that facilitates gene expression in the host cell may be used. Such control elements can include control sequences normally associated with the selected exogenous nucleic acid or nucleic acids encoding Rep and Cap. Alternatively, heterologous control sequences can be employed.

To achieve appropriate levels of AAV proteins and Ad transcription products, any of a number of promoters suitable for use in the selected host cell may be employed. For example, constitutive promoters of different strengths can be used to express the different AAV proteins. Inducible promoters may also be used in compositions and methods of the invention. To achieve regulated expression of AAV proteins, the AAV p5 and p19 promoters are preferred. Other promoters for use in the invention include both non-viral and viral promoters. Non-viral promoters that may be used include β-actin and Factor IX promoters. Examples of viral promoters include cytomegalovirus immediate early promoter (CMV), simian virus 40 (SV40) late promoter, Mouse Mammary Tumor Virus (MMTV) promoter (Grimm et al., Hum. Gene Ther. 9:2745–2760, 1998) and Ad E1A promoter.

In some applications, vectors of the invention contain a selectable marker gene used to identify cells that contain the vector. Suitable selectable marker genes for use in the invention include genes encoding enzymes that produce antibiotic resistance (e.g., those conferring resistance to ampicillin, penicillin, kanamycin, hygromycin, G418, or streptomycin), as well as those that encode enzymes that result in a calorimetric or fluorescent signal (e.g., green fluorescent protein, β-galactosidase).

Cells Containing Nucleic Acid Molecules of the Invention

The invention provides a cell containing a nucleic acid molecule having a nucleotide sequence encoding an AAV Rep protein of a first serotype, a nucleotide sequence encoding an AAV Cap protein of a second serotype, and a nucleotide sequence encoding a transcription product having at least one Ad helper function. A cell according to the invention is any cell in which the nucleotide sequences can be expressed resulting in expression products (e.g., polypeptides, RNA molecules). Cells of the invention may be non-mammalian cells (e.g., microorganisms, yeast cells, insect cells) or mammalian cells (e.g., human cells). A cell according to the invention can further contain a second nucleic acid molecule containing a polynucleotide to be expressed interposed between two AAV ITRs. Typically, both nucleic acid molecules are present within a vector (e.g., plasmid). Preferred cells are those in which pseudotyped virions are formed based on the presence of the two nucleic acid molecules. Examples of useful cells for expressing nucleotide sequences resulting in the formation of pseudotyped rAAV virions include 293 (Graham et al., J. Gen. Virol. 36:59–72, 1977), HeLa (Bantel-Schaal et al., J. Virol. 73:939–947, 1984), and KB (Srivastava, A. Intervirology 27:138–147, 1987) cells.

Ad Helper Function

The invention encompasses nucleotide sequences encoding transcription products (e.g., polypeptides, RNA) having at least one Ad helper function. AAV is a helper-dependent virus, and as such, it requires co-infection with a helper virus such as Ad or cotransfection of helper virus DNA for a productive infection. See Ward and Berns, J. Virol., 70:4495, 1996. Nucleotide sequences encoding transcription products having Ad, helper function utilized in the present invention may be derived from any of a number of Ad serotypes that facilitate AAV infection. For example, sequences derived from Ad serotype 5 (Ad5) can be used. Preferably, nucleotide sequences encoding transcription products having Ad helper function reside in plasmids pXYZ1 and pXYZ5 for the generation of pseudotyped rAAV virions.

AAV Serotypes rAAV vectors and virions useful in the invention include those derived from a number of AAV serotypes, including 1, 2, 3, 4, 5, 6, and 7. Because of wide construct availability and extensive characterization, preferred rAAV vectors for use in the invention are those derived from serotype 2 (or mutants thereof). In methods of encapsidating rAAV2 vector contructs, use of serotype 2 Rep proteins is preferred. Because of tissue tropisms and purification methods described herein, preferred AAV Cap proteins are those derived from serotypes 1 and 5. Construction and use of AAV vectors and AAV proteins of different serotypes are discussed in Chao et al., Mol. Ther. 2:619–623, 2000; Davidson et al., PNAS 97:3428–3432, 2000; Xiao et al., J. Virol. 72:2224–2232, 1998; Halbert et al., J. Virol. 74:1524–1532, 2000; Halbert et al., J. Virol. 75:6615–6624, 2001; and Auricchio et al., Hum. Molec. Genet. 10:3075–3081, 2001.

The invention also relates to the production of pseudotyped rAAV virions that have mutations within the virion capsid. For example, suitable AAV mutants may have ligand insertion mutations for the facilitation of targeting AAV to specific cell types. The construction and characterization of AAV capsid mutants including insertion mutants, alanine screening mutants, and epitope tag mutants is described in Wu et al., (J. Virol. 74:8635–45, 2000). Other rAAV virions that can be generated in methods of the invention include those capsid hybrids that are generated by molecular breeding of viruses as well as by exon shuffling. See Soong et al., Nat. Genet. 25:436–439, 2000; and Kolman and Stemmer Nat. Biotechnol. 19:423–428, 2001.

Producing Pseudotyped rAAV Virions

The nucleic acid molecules of the invention are useful in methods of producing pseudotyped rAAV virions. In a method of producing rAAV virions, a cell containing two nucleic acid molecules, the first nucleic acid molecule having a nucleotide sequence encoding an AAV Rep protein of a first serotype, a nucleotide sequence encoding an AAV Cap protein of a second serotype, and a nucleotide sequence encoding a transcription product having at least one Ad helper function, the second nucleic acid molecule having an exogenous nucleic acid interposed between two AAV ITRs, is placed in in vitro conditions. These in vitro conditions are such that the first nucleic acid molecule is expressed, the second nucleic acid molecule is replicated, and rAAV virions are produced. Placing the cell in in vitro conditions includes placing the cell into a culture medium (e.g., DMEM supplemented with fetal bovine serum and antibiotics) in a humidified incubator (e.g., 5% $CO_2$) at a suitable temperature (e.g., 37°). In the second step of this method, the rAAV virions produced in the cell are isolated. To isolate produced rAAV virions, the cell is separated from the medium, the cell is then lysed to yield a cell lysate, and the virions are isolated from the cell lysate. To separate the rAAV virions from the cell lysate, the rAAV virions are subjected to a density gradient separation step, such as an iodixanol step gradient. The virions can be further isolated (e.g., purified) by subjecting the virions to an additional purification step such as an ion exchange (e.g., anion exchange) chromatography step. Typically, a cell used in the method is a mammalian cell (e.g., 293 cells). In some applications, the rAAV virions produced contain at least one AAV serotype 1 capsid protein. In other applications, the rAAV virions produced contain at least one AAV serotype 5 capsid protein.

To generate cells containing the nucleic acids described above, the nucleic acids are introduced into the cells. To introduce nucleic acid molecules into a suitable host cell, a number of known transfection techniques may be used. See, e.g., Graham et al., (Virology 52:456, 1973), Sambrook et al., supra, Chu et al., (Gene 13:197, 1981). Particularly suitable transfection methods include calcium phosphate co-precipitation (Graham et al., Virol. 52:456–467, 1973), direct micro-injection into cultured cells (Capecchi, M. R. Cell 22:479–488, 1980), electroporation (Shigekawa et al., BioTechniques 6:742–751, 1988), liposome mediated gene transfer (Mannino et al., BioTechniques 6:682–690, 1988), lipid-mediated transduction (Felgner et al., PNAS 84:7413–7417, 1987), and nucleic acid delivery using high-velocity microprojectiles (Klein et al., Nature 327:70–73, 1987).

Purification of rAAV Virions

The invention provides methods for purifying pseudotyped rAAV virions. Methods of the invention involve applying a virus-containing sample to one or more purification steps, including density gradient separation and chromatography. An example of a method for purifying rAAV virions includes several steps. First, a plurality of cells infected with rAAV virions is provided. From these infected cells, rAAV virions are collected. These virions are then subjected to a density gradient separation step such as one using an iodixanol gradient. A typical iodixanol step gradient contains a 15% iodixanol step, a 25% iodixanol step, a 40% iodixanol step, and a 60% iodixanol step. The iodixanol step can further include 1M NaCl. The virion-containing iodixanol step is centrifuged, and the resultant virion-containing sample is collected from the iodixanol gradient step. This sample is then subjected to a chromatography step, such as an ion exchange or hydroxyapatite chromatography step.

Purification methods of the invention are particularly useful for purifying virions having capsids containing proteins from AAV serotypes 1 and 5 because these serotypes do not bind to heparin columns. To purify rAAV1 and rAAV5 virions, purification protocols are employed that use iodixanol density gradient centrifugation followed by anion exchange or hydroxyapatite chromatography. Iodixanol is an iodinated density gradient media originally produced as an X-ray contrast compound for injection into humans. Unlike the hyper-osmotic inorganic salt (CsCl) and sucrose gradients commonly used for fractionating macromolecules, iodixanol solutions can be made iso-osmotic at all densities. This property makes iodixanol an ideal media for analysis and downstream purification steps. In addition, iodixanol has the capacity to separate free capsid proteins and empty capsids from vector genome-containing (full) capsids. Although the use of iodixanol is preferred in the invention, other suitable density gradient media might be substituted.

Following density gradient centrifugation, rAAV vectors are purified by column chromatography. Any chromatography method that allows purification of rAAV virions may be used. For example, ion exchange chromatography can be used. Ion exchange chromatography is a method that relies on charge interactions between the protein of interest and the ion exchange matrix, which is generally composed of resins, such as agarose, dextran, and cross-linked cellulose and agarose, that are covalently bound to a charged group. Charged groups are classified according to type (cationic and anionic) and strength (strong or weak). Ion exchange chromatographic techniques generally take place in several steps: equilibration of the column to pH and ionic conditions ideal for target protein binding, reversible adsorption of the sample to the column through counterion displacement, introduction of elution conditions that change the buffer's pH or ionic strength in-order to displace-bound proteins, and elution of substances from the column in order of binding strength (weakly-bound proteins are eluted first). Ion exchange chromatography is directly upgradable from a small-scale to a bulk-scale level. Anionic exchange chromatography is a type of ionic exchange chromatography in which a negatively charged resin will bind proteins with a net positive charge. Examples of commercially available anion-exchange resins include HiTrapQ by Pharmacia; MonoQ, MonoS, MiniQ, Source 15Q, 30Q, Q Sepharose, DEAE, and Q Sepharose High Performance by Amersham Biosciences (Piscataway, N.J.); WP PEI, WP DEAM, and WP QUAT by J. T. Baker (St. Louis, Mo.); Hydrocell DEAE, and Hydrocell QA by Biochrom Labs (Terre Haute, Ind.); UNOsphere Q, Macro-Prep DEAE, and Macro-Prep HighQ by Bio-Rad (Hercules, Calif.); Ceramic HyperD Q, Ceramic HyperD S, Ceramic HyperD DEAE, Trisacryl M DEAE, Trisacryl LS. DEAE, Spherodex LS DEAE, QMA Spherosil, and QMA M Spherosil by Ciphergen (Fremont, Calif.); DOWEX MONOSPHERE by Dow Liquid Separations (Midland, Mich.); Matrex Q500, Matrex A500, Matrex Q800, Matrex A800, and Matrex A200 by Millipore (Bedford, Mass.); Fractogel EMD TMAE, Fractogel EMD DEAE, and Fractogel EMD DMAE by Novagen (Madison, Wis.); Amberlite Strong Anion Exchangers Type I, Amberlite Strong Anion Exchangers Type II, DOWEX Strong Anion Exchangers, Type I, DOWES Strong Anion Exchangers Type II, Diaion Strong Anion Exchangers Type I, Diaion Strong Anion Exchangers Type I, Diaion Strong Anion Exchangers Type II, Amberlite Weak Anion Exchangers, and DOWEX Weak Anion Exchangers by Sigma-Aldrich (St. Louis, Mo.); TSK Gel DEAE-5PW-HR, TSK Gel DEAE-5PW, TSK Gel Q-5PW-HR, and TSK Gel Q-5PW by Tosoh Biosep (Montgomeryville, PA); and QA52, DE23, DE32, DE51, DE52, DE53, Express-Ion D and Express-Ion Q by Whatman (Kent, UK). For the purification of rAAV1 and rAAV5 virions, anion-exchange chromatography is preferred.

Figure 3:
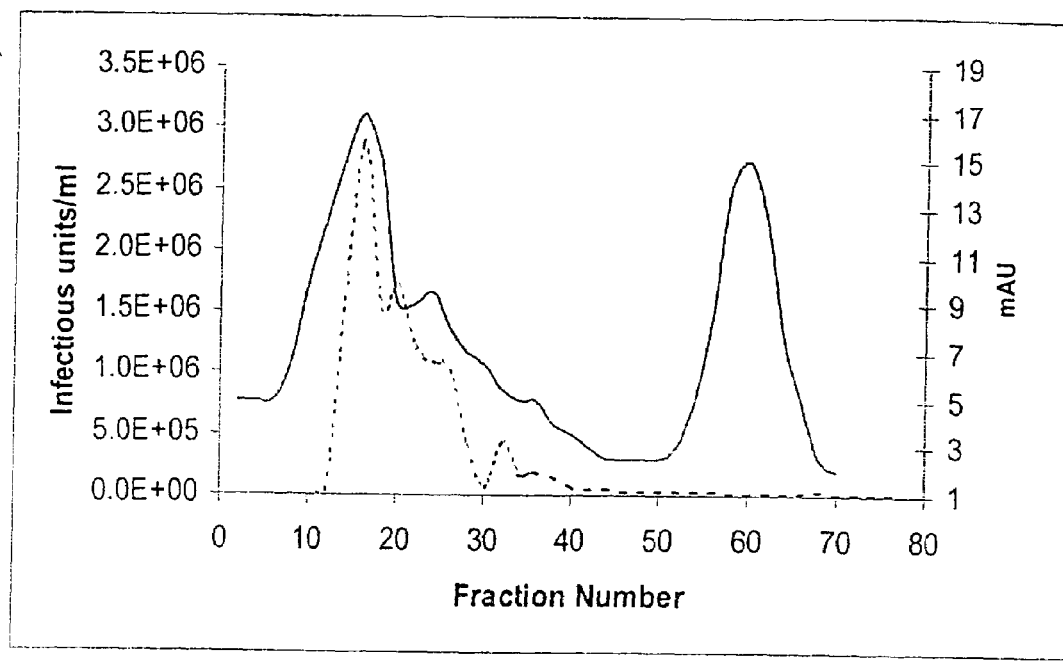
FIGS. 3A and B are chromatograms of rAAV virions purified by anion exchange and hydroxyapatite chromatography.
Figure 3:
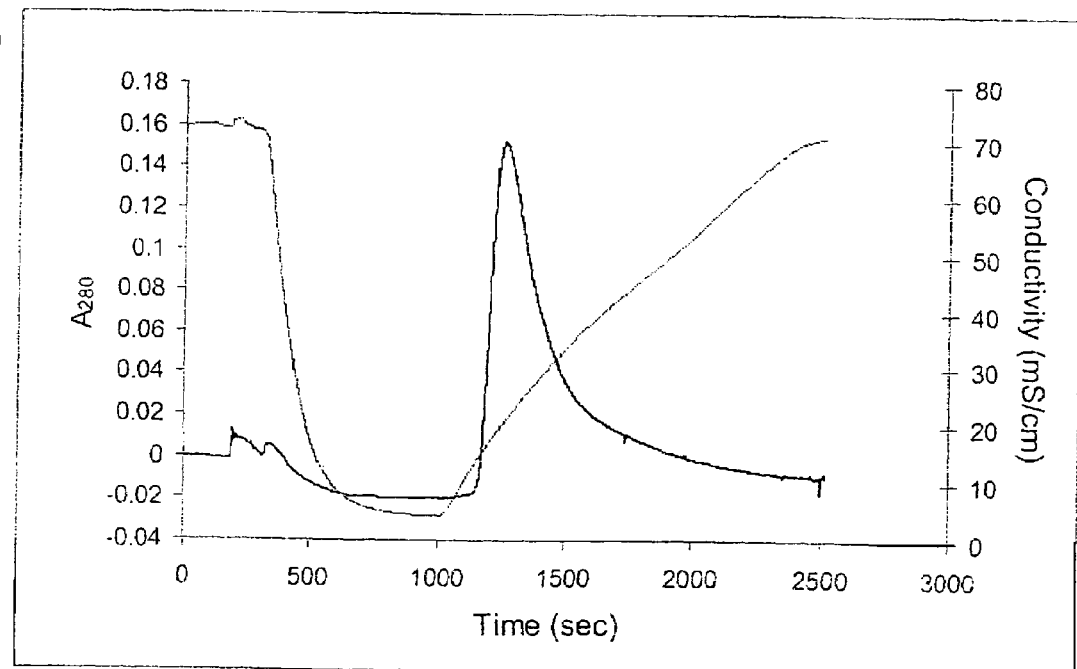

Hydroxyapatite chromatography is another example of a suitable chromatography technique. Hydroxyapatite is a crystalline form of calcium phosphate. The mechanism of hydroxyapatite chromatography involves nonspecific interactions between negatively charged protein carboxyl groups and positively charged calcium ions on the resin, and positively charged protein amino groups and negatively charged. phosphate ions on the resin. Examples of commercially available hydroxyapatite resins include Bio-Gel HT and CHT ceramic resins by Bio-Rad (Hercules, Calif.); hydroxylapatite high resolution and hydroxylapatite fast flow by Calbiochem (San Diego, Calif.); HA Ultrogel by Ciphergen (Fremont, Calif.); and hydroxyapatite by Sigma-Aldrich (St. Louis, Mo.). In addition to anion exchange chromatography; rAAV5 virions,: were purified using hydroxyapatite chromatography (FIG. 3B). An example of a preferred hydroxyapatite resin is ceramic hydroxyapatite by Bio-Rad, Hercules, Calif., as this is a, stable, porous form of hydroxyapatite with an improved calcium:phoshpate ration, which overcomes low binding capacity due to excess phoshpate.

For the purification of rAAV2 virions, heparin-agarose chromatography is preferred (FIG. 3A). See, e.g, U.S. Pat. No. 6,146,874.

A combination of iodixanol step gradient followed by either affinity heparin (for purifying rAAV2), hydroxyapatite, or anion exchange chromatography (for purifying AAV1, 2 and 5) is used to facilitate the high-throughput of several viruses for direct comparison of transduction efficiency and specificity in animal models and cell culture. Scaled-up production of the viruses in tissue culture is facilitated by the use of cell factories, e.g., plastic trays with large culture surface areas (Nunc, Rochester, N.Y.). More importantly, purification of rAAV1, 2 and 5 virions on Q-Sepharose allows the comparison of virions purified using the same method. Furthermore, the cell-factory based protocol results in virion stocks with titers of $1 \times 10^{12}$–$1 \times 10^{13}$ vg/ml purified from $1 \times 10^9$ cells. These chromatographic methods have the added benefit that they can be readily scaled up to purify virus from $1 \times 10^{10}$ cells.

By optimizing the transfection protocol and the method of purification, 100–200 infectious units (IU) per cell can routinely be obtained. For a preparation from $1 \times 10^9$ cells, for example, the final yield of rAAV is approximately $1$–$5 \times 10^{11}$ IU or approximately $1 \times 10^{12-1 \times 10^{13}}$ vector genomes, with P:I ratios that average 20 and rarely exceed 100.

Virions are also purified using chromatography in the absence of density gradient centrifugation. As an example, lysates from infected cells can be directly subjected to chromatography for purification of rAAV virions. For large-scale production methods of rAAV vectors involving chromatography, see Potter et al. (Methods Enzymol. 346:413–430, 2002).

EXAMPLES

The present invention is further illustrated by the following specific examples. The examples are provided for illustration only and are not to be construed as limiting the scope or content of the invention in any way.

Example 1

Materials and Methods

AAV helper plasmids were constructed by combining the ORF coding for the AAV2 Rep proteins and the ORF coding for capsid proteins of serotypes 1 and 5. The pACG2R1C helper plasmid was constructed by substituting the AAV1 cap ORF for AAV2 cap ORF in pACG2 (Li et al., J. Virol. 71:5236–5243, 1997) and a similar approach was applied to the pACG2R5C plasmid. Rep2cap1 and rep2cap5 helper cassettes were then subcloned into an Ad helper plasmid, pXYZ, constructed from pAdEasy. To construct pXYZ, several Ad genes (penton, core protein, hexon, and Ad DNA polymerase) were disrupted and the left hand end of the Ad genome was removed to eliminate the possibility of generating infectious Ad and Ad structural proteins (some of which are cytotoxic). The resultant plasmids pXYZ1 and pXYZ5 (FIG. 1) were used to pseudotype AAV2-ITR-containing expression cassettes into AAV1 and AAV5 capsids, respectively.

Construction of pXYZ1 and pXYZ5 Helper Plasmids pXYZ Ad helper plasmid. Plasmid pAdEasy-1 (Stratagene, La Jolla, Calif.) was digested with SgfI and PmeI, the SgfI 3'-overhang was removed by treatment with T4 DNA-polymerase, and blunt ends were ligated to produce pAdEasyDel1. Upon digestion with ClaI and SalI, the 18.9 Kbp fragment was subcloned into pBlueScriptKS(–) to derive the pXYZ Ad helper plasmid.

pACG2R1C and pACG2R5C pseudotyping plasmids. wtAAV1 DNA (Genbank Accession no. NC_002077) and pAAV5-2 (Chiorini et al., J. Virol. 73:1309–1319, 1999) were used to amplify the ORFs coding for the capsid proteins of AAV1 and AAV5, respectively. For the AAV1 cap ORF primers, 5'GAGCAATAAATGATTTAAACCAG-GTATG3' (SEQ ID NO:1) and 5'GCTCTAGACCCGAT-GACGTAAGTCTTTTATCG3' (SEQ ID NO:2) were used, and for the AAV5 cap ORF primers, 5'GCCAATAAAGAA-CAGTAAATAATTTAAATAGTCAT GTCTTTTGTTGATCACC3' (SEQ ID NO:3) and 5'GGT-GATCAACAAAAGACATGACTATTTAAATTATTTACT GTTCTTTATTGGC3' (SEQ ID NO:4) were used. Upon digestion of the PCR fragments with DraI and XbaI, the resulting products were subcloned into pACG2 (Li et al., J. Virol. 71:5236–5243, 1997) and digested with SwaI and XbaI. The hybrid plasmids pACG2R1C and pACG2R5C contain the ORF coding for the AAV2 Rep proteins, and the ORF coding for either AAV1 or AAV5 capsid proteins, respectively.

pXYZ1 and pXYZ5 helper plasmids. XbaI fragments containing the rep-cap ORFs from pACG2R1C and pACG2R5C were subcloned into the XbaI site of pXYZ to derive pXYZ1 and pXYZ5, respectively. These helper plasmids encode the AAV and Ad genes required to pseudotype AAV2 ITR-containing nucleic acids into AAV1 or AAV5 capsids.

Construction of rAAV Vector Plasmids rAAV vector constructs were assembled using the pTR-UF backbone (Klein et al., Exp. Neurol. 150:183–194, 1998; and Zolotukhin et al., J. Virol. 70:4646–4654, 1996), thereby containing ITRs from AAV2.

Cell Transfection

Cell and virus processing was performed exclusively in biosafety cabinets during open steps. 293 cells (Graham et al., J. Gen. Virol. 36:59–72, 1977) were cultured in DMEM supplemented with 5% Fetal Bovine Serum and antibiotics (i.e., DMEM-complete). PBS and 0.05% trypsin were used during cell passage. Briefly, 293 cells were split 1:3 the day prior to transfection, so at the time of transfection the cell confluency was ~75–80%. A production run utilized about $1 \times 10^9$ cells seeded in a Cell Factory (Nunc, Rochester, N.Y.). The $CaPO_4$-precipitate was formed by mixing 1.8 mg of pDG (Grimm et al., Hum. Gene Ther. 9:2745–2760, 1998), pXYZ1, or pXYZ5, and 0.6 mg of the rAAV vector plasmid (~1:1 molar ratio) in a total volume of 50 ml of 0.25 M $CaCl_2$ followed by the addition of 50 ml of 2×HBS pH 7.05 to the DNA/$CaCl_2$ (Snyder et al., Production of Recombinant Adeno-Associated Viral Vectors, In N. Dracopoli, J. Haines, B. Krof, D. Moir, C. Morton, C. Seidman, J. Seidman, and D. Smith, Current Protocols in Human Genetics, John Wiley and Sons: New York, N.Y. 1996). The mixture was incubated for 1 min at room temperature, at which time the formation of precipitate was stopped by diluting the mixture into 1100 ml of pre-warmed DMEM-complete. The conditioned culture media was removed from the cells and the fresh precipitate-containing media was added immediately. Cells were incubated at 37° C., 5% $CO_2$ for 60 hrs and the $CaPO_4$ precipitate was allowed to remain on the cells during this incubation period. At the end of the incubation the culture media was discarded, cells were washed with PBS, and harvested using PBS containing 5 mM EDTA. The collected cells were centrifuged at 1000×g for 10 minutes, resuspended in 60 ml Lysis Solution (150 mM NaCl, 50 mM Tris pH 8.4), combined, and stored at −20° C. until purified.

Cell Lysate and Iodixanol Gradients

Cells were lysed by 3 freeze/thaw cycles between dry ice-ethanol and 37° C. water baths. Other methods for lysing cells might also be used, e.g., microfluidization. Benzonase (Sigma, St. Louis, Mo.) was then added to the cell lysate (50

U/ml final concentration) and incubated for 30 min at 37° C. The crude lysate was clarified by centrifugation at 4000×g for 20 minutes and the virus-containing supernatant was divided between four iodixanol gradients.

Discontinuous iodixanol step gradients were formed in quick seal tubes (25×89 mm, Beckman, Fullerton, Calif.) by underlaying and displacing the less dense cell lysate (15 ml) with iodixanol prepared using a 60% (w/v) sterile solution of OptiPrep (Nycomed, Roskilde, Denmark) and PBS-MK buffer (1×PBS containing 1 mM $MgCl_2$ and 2.5 mM KCl). Therefore, each gradient consisted of (from the bottom): 5 ml 60%, 5 ml 40%, 6 ml 25%, and 9 ml of 15% iodixanol; the 15% density step also contained 1 M NaCl. Tubes were sealed and centrifuged in a Type 70 Ti rotor at 69,000 rpm (350,000×g) for 1 hr at 18° C. Approximately 5 ml of the 60%-40% step interface was aspirated after side-puncturing each tube with a syringe equipped with an 18-gauge needle. The iodixanol band from each of the four gradients was combined; this could be frozen until column chromatography was performed.

rAAV Column Chromatography

The iodixanol gradient fraction was further purified and concentrated by column chromatography. For AAV2 virions, a 3 ml heparin agarose Type I column (Sigma, St. Louis, Mo.) was equilibrated with 10 ml of PBS-MK buffer, then 10 ml of PBS-MK/1M NaCl, followed by 20 ml of PBS-MK buffer. The virus-containing iodixanol fraction (20 ml) was loaded onto the column by gravity flow. The column was washed with 20 ml of PBS-MK buffer and eluted in 15 ml of PBS-MK/1M NaCl. Alternatively, the AAV2 virions were purified using a 1 ml or 5 ml HiTrap Heparin column (Pharmacia) on an ATKA FPLC system (Pharmacia) run at 1 column volume per minute. The virus was then concentrated and desalted in a Biomax 100K concentrator (Millipore, Bedford, Mass.) by three cycles of centrifugation. In each cycle the virus was concentrated to 1 ml following the addition of 10 ml of Lactated Ringer's or 1×PBS. The virus was stored at −80° in Lactated Ringer's or 1×PBS.

For rAAV 1, 2, and 5 virions, a 5 ml HiTrap Q column (Pharmacia) was equilibrated at 5 ml/min with 5 column volumes (25 ml) of Buffer A (20 mM Tris, 15 mM NaCl, pH 8.5), then by 25 ml Buffer B (20 mM Tris, 500 mM NaCl, pH 8.5), followed by 25 ml of Buffer A using a Pharmacia ATKA FPLC system. The 20 ml virus-containing iodixanol fraction was diluted 1:1 with Buffer A and applied to the column at a flow rate of 3–5 ml/min. After loading the sample, the column was washed with 10 column volumes (50 ml) of Buffer A. The virus was eluted with Buffer B and 2 ml fractions were collected.

For rAAV5 virions, a buffer exchange and concentration of the vector-containing iodixanol fraction was performed using a Millipore (Bedford, Mass.) BioMax 50 filter device and 50 mM Tris pH 7.5. A Bio-scale Q5 (5 ml bed volume) CHT type I hydroxyapatite column (BioRad, Hercules, Calif.) was equilibrated with 5 ml Buffer C (20 mM potassium phosphate pH 7.5), then 7 ml Buffer D (500 mM Potassium phosphate pH 7.5), followed by 7 ml Buffer C at 1 ml/min using a BioRad (Hercules, Calif.) Biologic Duoflow system. Virus was loaded onto the column at 1 ml/min and the column was washed with 7 ml Buffer C, and eluted with a 25 ml linear gradient of 0–100% Buffer D followed by 7 ml 100% Buffer D. The virus eluted with 0.2M K-phosphate.

Quality Control Assays

Assay for protein purity of rAAV stocks. Virion stocks were analyzed by silver staining following electrophoresis on 10% SDS polyacrylamide gels. Western blotting was performed using the anti-AAV2 capsid monoclonal antibody B1 (American Research Products, Belmont, Mass.) at 1:2000. This antibody also recognizes the AAV1 and AAV5 capsid proteins (Wobus et al., J. Virol. 74:9281–9293, 2000). Detection was carried out using horseradish peroxidase (HRP)-conjugated sheep anti-mouse (Amersham, Piscataway, N.J.) at 1:5000 and Super Signal (Pierce, Rockford, Ill.).

Figure 5:
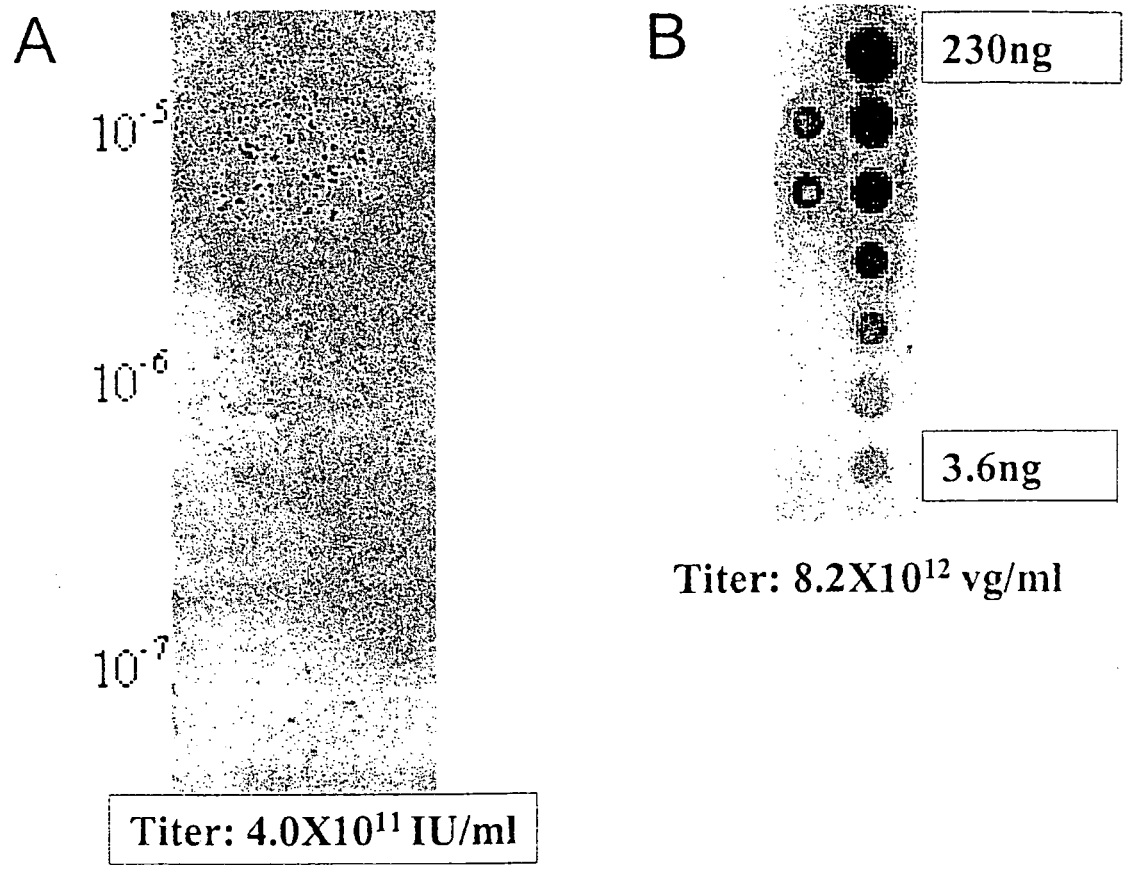
FIGS. 5A and B are infectious center and dot blot assays. A. The infectious center assay was performed on a rAAV2-GFP stock using a green fluorescent protein (GFP) probe. The values of the rAAV ten-fold dilution series is shown on the left side. The calculated infectious titer is shown below the blot. B. The dot blot assay was performed on the same rAAV2-GFP vector stock. Amounts (ng) of the relevant rAAV plasmid used to construct a two-fold standard curve are shown on the right side. The calculated titer (vector genome (vg)/ml) is shown below the blot. The particle:infectivity (P:I) ratio for this preparation is 20.5.

Assays for infectious rAAV. Stocks were assayed for infectious rAAV by the infectious center assay (ICA). In this assay, 96-well plates seeded with $2 \times 10^4$ C12 cells were infected 16 hours after seeding with 10-fold dilutions of rAAV and superinfected with WT Ad5 at a multiplicity of infection (MOI) of 10. Cells that had been infected by rAAV were then complemented for DNA replication and amplification of the rAAV genomes. Cells were harvested and suspended in 5 ml of 1×PBS, vacuum filtered onto nylon membranes (0.45 μm), and lysed with 0.5N NaOH/1.5M NaCl (this step also denatured and immobilized the DNA to the membrane) followed by neutralization with 1M Tris-HCl pH 7.0/2×SSC (20×SSC is 3M NaCl and 0.3M NaCitrate pH 7.0). The immobilized DNA was probed for transgene DNA (i.e., exogenous DNA) and only those cells that had been productively infected with rAAV produced a spot. The assay was accurate in the range of 10–200 spots (or infectious centers) per filter (FIG. 5A).

Additionally, a single cell fluorescence assay (SCFA) was used to determine the infectious titer of rAAV virus that expressed GFP. In this assay, $2 \times 10^4$ 293 or C12 cells in 96-well plates were infected with serial dilutions of a rAAV-GFP virus and co-infected with Ad5 (MOI of 10) to increase the sensitivity (Ferrari et al., J. Virol 70:3227–3234, 1997). Thirty hours later, cells infected with rAAV-GFP were visually scored using a fluorescence microscope and the titer was calculated according to the dilution factor. The titers obtained by SCFA were consistent (within a factor of 2) with those obtained by ICA.

Dot blot assay to determine the titer of rAAV physical particles and the particle to infectivity ratio. The dot blot assay was used to determine the titer of rAAV virions that contained vector genomes (FIG. 5B). Plasmid and unpackaged vector DNA was digested for 1 hour at 37° C. in a final volume of 200 ul containing 5U of DNaseI (Roche, Basel, Switzerland), 10 mM Tris-HCl, pH 7.5, and 1 mM $MgCl_2$. Encapsidated rAAV vector genomes were liberated by adding an equal volume of 2× proteinase K buffer (20 m M Tris-Cl, pH 8.0, 20 mM EDTA, pH 8.0, 1% SDS) followed by the addition of proteinase K (100 ug), and incubated at 37° C. for 1 hour. The liberated vector DNA was phenol extracted and ethanol precipitated. Precipitated DNA was dissolved in 40 ul of $dH_2O$ and diluted into 400 ul 0.4N NaOH/10 mM EDTA immediately prior to immobilization. A two-fold dilution series of the plasmid DNA that was packaged was prepared in water and diluted into 400 ul 0.4N NaOH/10 mM EDTA immediately prior to immobilization. Denatured vector DNA was immobilized onto a nylon membrane along with the plasmid standard curve using a dot blot apparatus (BioRad, Hercules, Calif.). The blots were probed for the transgene and exposed to film or Phosphorimager screen (Molecular Dynamics, Piscataway, N.J.). The vector DNA signal was compared to the signal generated from the plasmid DNA standard curve, and extrapolated to determine a vector genome titer. A comparison of the vector genome titer to the ICA titer produced the P:I ratio.

Performance of purified rAAV 1, 2, and 5 virions. Purified serotype virions were used to transduce cells in culture. Vector performance evaluation results are described below in Example 6.

Example 2

Purification of rAAV1 and 5 Virions

Because AAV1 and AAV5 both lack significant binding to the heparin affinity resin used to purify rAAV2 virions, purification protocols were developed that use density gradient centrifugation followed by anion exchange or hydroxyapatite chromatography.

Figure 4:
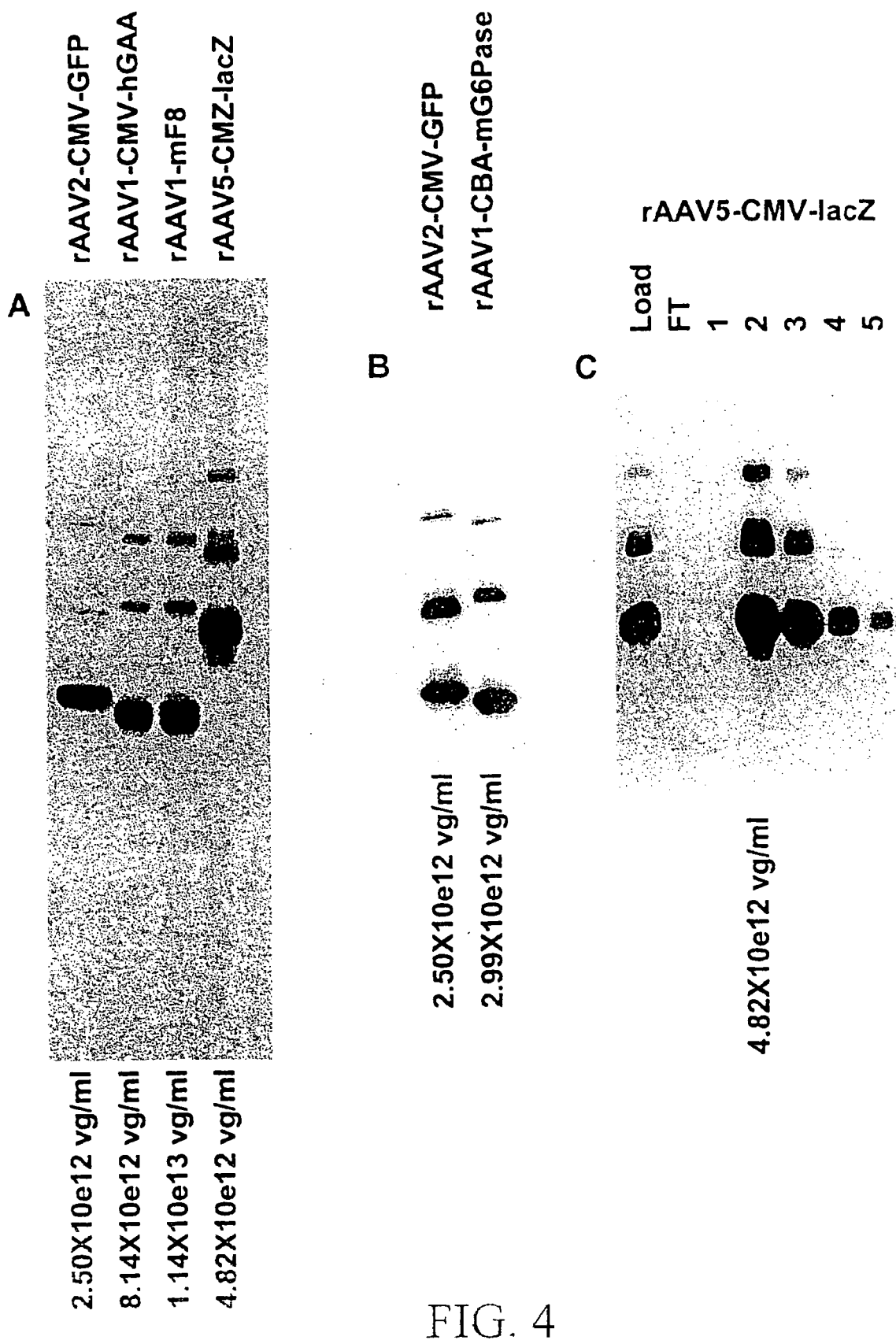
FIGS. 4A, B, and C are gels characterizing rAAV virion stocks. A. Silver-stained sodium dodecyl sulfate polyacrylamide gel electrophoresis (SDS-PAGE) gel of rAAV1, 2, and 5 virion stocks (10 ul per lane). The titers of rAAV stocks are shown below each lane. B. Western blot analysis of rAAV1 and 2 virion stocks (10 ul per lane). C. Profile of anion exchange chromatography of an AAV5 virus (10 ul of each fraction per lane). Load is the iodixanol gradient purified material that was applied to the column; FT is the flow through, 1–5 are fractions eluted from the column. Monoclonal antibody B1 was used to detect AAV capsid proteins in Panels B and C.

Following density gradient centrifugation, rAAV virions were purified by column chromatography. Three column resins were used: heparin-agarose, Q-sepharose, and hydroxyapatite. AAV2 virions bound heparin-agarose (FIGS. 6A and B), AAV5 virions bound hydroxyapatite, and AAV1, 2, and 5 virions bound Q-Sepahrose (FIGS. 3A and 4). rAAV2 virions eluted from heparin with 0.35M NaCl and rAAV5 virions eluted from hydroxyapatite with 0.2 M phosphate. AAV 1, 2, and 5 eluted from Q-Sepharose in 0.5 M NaCl. As shown in FIG. 6A, virions produced were 99% pure with the three capsid proteins at the proper ratio of ~1:1:20 for VP1:VP2:VP3. A combination of iodixanol step gradient followed by either affinity Heparin (for purifying rAAV2), hydroxyapatite (for purifying AAV5), or anion exchange chromatography (for purifying AAV1, 2 and 5) was used to facilitate the high throughput of several viruses for direct comparison of transduction efficiency and specificity in animal models and cell culture. Scaled-up production of the virus in tissue culture was facilitated by the use of cell factories, e.g., plastic trays with large culture surface areas (Nunc, Rochester, N.Y.). Purification of rAAV1, 2 and 5 virions on Q-Sepharose allowed the comparison of virions purified using the same method. Furthermore, the cell-factory based protocol resulted in virus stocks with titers of $1\times10^{12}-1\times10^{13}$ vg/ml purified from $1\times10^9$ cells. These chromatographic methods have the added benefit that they can be readily scaled up to purify vector from $1\times10^{10}$ cells.

By optimizing the transfection protocol and the method of purification, 100–200 IU per cell can routinely be obtained. For a preparation from $1\times10^9$ cells, this means that the final yield of rAAV is approximately $1-5\times10^{11}$ IU or approximately $1\times10^{12}-1\times10^{13}$ vector genomes, with P:I ratios that average 20 and rarely exceed 100. Previous preparations that relied on CsCl centrifugation had average P:I ratios that were often greater than 200 and sometimes as high as 10,000.

Example 3

ICA For rAAV and rcAAV

The infectious titer of rAAV was determined by measuring the ability of the virus to infect C12 cells expressing AAV2 rep and cap ORFs, unpackage, and replicate (FIG. 5A). In this assay, rep-cap expressing C12 cells were infected with serial dilutions of rAAV. To score the infecting viral particle it was amplified through viral DNA replication, whereupon the number of viral genomes reached several thousand per cell. This amplification was achieved by co-infecting the cell with a saturating amount of Ad5 to initiate rep and cap gene expression required for AAV DNA replication. The cells were then incubated for 40 hours, harvested, and transferred onto a nylon membrane and lysed. The immobilized viral DNA was hybridized with a transgene-specific probe and the cells infected with rAAV particles were scored as black dots following autoradiography (FIG. 5A).

WT AAV may contaminate vector preparations, and rcAAV may be formed during the production of rAAV due to recombination between the rAAV genome and the AAV helper plasmid. Since expression of the AAV rep gene has been shown to affect transduction frequency (McLaughlin et al., J. Virol. 62:1963–1973, 1988; and Samulski et al., J. Virol. 63:3822–3828, 1989) and gene expression (Horer et al., J. Virol. 69:5485–5496, 1995; and Labow et al., J. Virol. 60:251–258, 1986), and possibly change the integration specificity of the provirus (Kearns et al., Gene Ther. 3:748–755, 1996; and Ponnazhagan et al., Hum. Gene Ther. 8:275–284, 1997), it was necessary to evaluate the extent of rcAAV or wtAAV contamination in rAAV virion stocks. A variation of the ICA allowed for the determination of wtAAV and rcAAV contamination. In this assay, 293 cells were infected with the rAAV and Ad, and the filters were hybridized with a AAV rep-cap probe. Only rep-cap expressing wtAAV or rcAAV was propagated in the presence of Ad and scored as black dots following autoradiography. The ICA was performed on a rAAV2-GFP vector using a GFP probe. The calculated infectious titer was $4.0\times10^{11}$ IU/ml.

Example 4

Dot Blot Assay to Determine Titer and Particle to Infectivity Ratio of rAAV Virions The dot blot assay was used to determine the titer of rAAV virions harboring vector genomes (FIG. 5B). This assay allowed direct comparisons of the potency of the different serotype virions administered to the same cell type. The dot blot assay was performed on the same rAAV2-GFP stock as that of Example 2. The calculated vg titer was $8.2\times10^{12}$ vg/ml.

Example 5

Performance of rAAV 1, 2, and 5 Virions rAAV1-GFP and rAAV5-GFP virions purified by Q-sepharose chromatography and rAAV2 virions purified by heparin chromatography were used to transduce rat oval cells in culture (FIG. 6). The rAAV5-GFP transduced rat oval cells more efficiently than either rAAV2-GFP or rAAV 1-GFP virions. Transduction of oval cells with rAAV vectors provides a therapeutic approach for treating liver disease or systemic protein deficiencies.

Example 6

In Situ Detection of GAA Activity in Tibialis Anterior (TA) Muscles From Gaa–/– Mice Glycogen storage disease type II (Gaa–/–) mice (Raben et al., J. Biol. Chem. 273:19086–19092, 1998), which lack the lysosomal hyrolase acid α-glucosidase, were injected intramuscularly under 2,2,2-tribromoethanol (Avertin) anesthesia. Mice were administered $4\times10^{10}$ vector genomes of rAAV1-CMV-mGaa, expressing the murine Gaa cDNA. For histochemical detection of GAA, muscle was snap-frozen in liquid nitrogen-cooled isopentane, followed by serial transverse sectioning (10 um), and processing was performed much as described by Sanes et al., (Embo J. 5:3133–3142, 1986) with the substitution of the substrate 5-bromo-4-chloro-3-indolyl-α-D-glucopyranoside (Calbiochem, San Diego, Calif.), which yielded an intense blue color upon cleavage by GAA, and counterstained with nuclear fast red. Gaa–/– TA muscle treated with AAV1-CMV-mGaa expressed detectable amounts of GAA, while untreated TA muscle from the contralateral leg of the same mouse did not.

Rat oval cells were isolated from male Fischer 344 rats (Petersen et al., Science 284:1168–1170, 1999; and Petersen et al., Hepatology 27:1030–1038, 1998). Briefly, a 2-acetylaminofluorene (2-AAF) tablet was inserted subcutaneously into the lower quadrant to suppress the hepatocyte proliferation. After 5–7 days a partial hepatectamy was performed to induce a severe hepatic injury. Seven days later the liver was perfused with a collagenase H solution. The oval cells were immediately sorted by fluorescence activated cell sorting (FACS) using a FITC-conjugated anti-rat Thy 1.1 antibody. The purified oval cells were then plated onto sixteen well chamber slides and infected with the rAAV1, 2, and 5 viruses (10,000 vector genomes/cell) or mock infected. Nine days after infection the cells were visualized by either bright-field or fluorescent microscopy for the expression of GFP using a Zeiss Axiovert microscope.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A nucleic acid molecule comprising:
   (A) a first nucleotide sequence encoding an AAV Rep protein of a first serotype;
   (B) a second nucleotide sequence encoding an AAV Cap protein of a second serotype generated by amplifying of SEQ ID NO's: 1–4 ; the second serotype being different from the first serotype; and
   (C) a third nucleotide sequence, encoding a transcription product containing an adenoviral sequence encoding a VA Adenoviral helper function, in reverse orientation to said first and second nucleotide sequences.

2. The nucleic acid molecule of claim 1, wherein the nucleic acid molecule is comprised within a vector.

3. The nucleic acid molecule of claim 1, wherein the AAV Rep protein is un AAV serotype 2 protein.

4. The nucleic acid molecule of claim 1, wherein the AAV Rep protein is Rep52.

5. The nucleic acid molecule of claim 1, wherein the AAV Rep protein is Rep78.

6. The nucleic acid molecule of claim 1, wherein the AAV Cap protein is an AAV serotype 1 Cap protein.

7. The nucleic acid molecule of claim 1, wherein the AAV Cap protein is an AAV serotype 5 Cap protein.

8. The nucleic acid molecule of claim 1, wherein the second nucleotide sequence encodes an AAV protein selected from the group consisting of: VP1, VP2, and VP3.

9. The nucleic acid molecule of claim 1, wherein the nucleic acid molecule further comprises a selectable marker.

10. The nucleic acid molecule of claim 2, wherein the nucleic acid is operably linked to at least one expression control sequence.

11. The nucleic acid molecule of claim 4, wherein the first nucleotide sequence additionally encodes a Rep78 protein.

12. The nucleic acid molecule of claim 8, wherein the second nucleotide sequence encodes VP1, VP2, and VP3.

13. The nucleic acid molecule of claim 10, wherein the first nucleotide sequence encoding an AAV Rep protein of a first serotype is operably linked to a promoter.

14. The nucleic acid molecule of claim 10, wherein the second nucleotide sequence encoding an AAV Cap protein of a second serotype is operably linked to a promoter.

15. The nucleic acid molecule of claim 10, wherein the third nucleotide sequence encoding the adenoviral VA helper function is operably linked to a promoter.

16. The nucleic acid molecule of claim 13, wherein the promoter is selected from the group consisting of: AAV p5 and AAV p19 promoters.

17. The nucleic acid molecule of claim 14, wherein the promoter is an AAV p40 promoter.

18. The nucleic acid molecule of claim 9, wherein the selectable marker confers antibiotic resistance to a cell.

19. A cell comprising a nucleic acid molecule said nucleic acid molecule comprising:
   (A) a first nucleotide sequence encoding an AAV Rep protein of a first serotype;
   (B) a second nucleotide sequence encoding an AAV Cap protein of a second serotype generated by amplifying SEQ ID NO's.: 1–4; the second serotype being different from the first serotype; and,
   (C) a third nucleotide sequence encoding a transcription product containing an adenoviral sequence encoding a VA Adenoviral helper function.

20. The cell of claim 19, wherein the cell is a mammalian cell.

21. The cell of claim 19, further comprising a second nucleic acid comprising a polynucleotide to be expressed interposed between a first AAV inverted terminal repeat and a second AAV inverted terminal repeat.

22. The cell of claim 21, wherein the second nucleic acid is comprised within a vector.

23. The cell of claim 21, wherein the polynucleotide encodes a protein.

24. The cell of claim 21, wherein the polynucleotide encodes a selectable marker.

25. The cell of claim 22, wherein the first AAV inverted terminal repeat is an AAV serotype 2 inverted terminal repeat.

26. The cell of claim 25, wherein the second AAV inverted terminal repeat is an AAV serotype 2 inverted terminal repeat.

27. The cell of claim 24, wherein the selectable marker is green fluorescent protein.

28. A method of producing rAAV virions, the method comprising the steps of:
   (a) culturing a cell comprising a nucleic acid molecule comprising: a first nucleotide sequence encoding an AAV Rep protein of a first serotype; a second nucleotide sequence encoding an AAV Cap protein of a second serotype generated by amplifying SEQ ID NO's.: 1–4; the second serotype being different from the first serotype; and, a third nucleotide sequence encoding a transcription product containing an adenoviral sequence encoding a VA Adenoviral helper function whereby, rAAV virions are produced; and,
   (b) isolating the rAAV virions produced from the cell.

29. The method of claim 28, wherein the cell is a mammalian cell.

30. The method of claim 28, wherein the step (a) comprises culturing the cell into a culture medium.

31. The method of claim 28, wherein the step (b) of isolating the rAAV virions produced from the cell comprises subjecting the produced rAAV virions to an iodixanol step gradient.

32. The method of claim 30, wherein the step (h) of isolating the rAAV virions produced from the cell comprises separating the cell from the medium, lysing the cell to yield a cell lysate, and then isolating the rAAV virions from the cell lysate.

33. The method of claim 31, further comprising subjecting the produced rAAV virions to ion exchange chromatography.

34. The method of claim 33, wherein the produced rAAV virions contain at least one AAV serotype 1 capsid protein.

35. The method of claim 33, wherein the produced rAAV virions contain at least one AAV serotype 5 capsid protein.

* * * * *

UNITED STATES PATENT AND TRADEMARK OFFICE
CERTIFICATE OF CORRECTION

| | | |
|---|---|---|
| PATENT NO. | : 7,094,604 B2 | Page 1 of 1 |
| APPLICATION NO. | : 10/798192 | |
| DATED | : August 22, 2006 | |
| INVENTOR(S) | : Snyder et al. | |

It is certified that error appears in the above-identified patent and that said Letters Patent is hereby corrected as shown below:

Col. 1, line 19, under STATEMENT AS TO FEDERALLY FUNDED RESEARCH, replace "The United States government may have certain rights in the invention" with --The government has certain rights in the invention--

Signed and Sealed this

Fifteenth Day of July, 2008

JON W. DUDAS
*Director of the United States Patent and Trademark Office*